United States Patent [19]

Alvarez et al.

[11] 4,055,564

[45] Oct. 25, 1977

[54] NOVEL PROSTAGLANDIN INTERMEDIATES AND PROCESS FOR THE PRODUCTION THEREOF

[75] Inventors: Francisco S. Alvarez, Sunnyvale; Albert R. Van Horn, Menlo Park, both of Calif.

[73] Assignee: Syntex (U.S.A.) Inc., Palo Alto, Calif.

[21] Appl. No.: 716,727

[22] Filed: Aug. 23, 1976

Related U.S. Application Data

[62] Division of Ser. No. 541,188, Jan. 15, 1975, Pat. No. 3,998,852, which is a division of Ser. No. 351,312, April 16, 1973, Pat. No. 3,886,185.

[51] Int. Cl.$^2$ .......................... C07D 7/02; C07C 61/06
[52] U.S. Cl. .............. 542/413; 260/345.8 P; 260/345.9 P; 260/586 R; 424/283; 424/305; 560/1; 560/231
[58] Field of Search .................. 260/240 R, 345.8 P, 260/345.9 P

[56] References Cited

U.S. PATENT DOCUMENTS

| 3,505,386 | 4/1970 | Babcock | 260/514 D |
| 3,751,463 | 8/1973 | Caton et al. | 260/345.8 |
| 3,867,377 | 2/1975 | Kluge et al. | 260/345.8 |

*Primary Examiner*—Arthur P. Demers
*Attorney, Agent, or Firm*—Gerard A. Blaufarb; William B. Walker

[57] ABSTRACT

Novel prostaglandin intermediates and process for the production thereof. Compounds, and process for the production thereof, useful in the production of (dl)-[1α-hydroxy-3β-(3S-tetrahydropyranyloxy-trans-1-octenyl)-4α-tetrahydropyranyloxy-cyclopent-1α-yl] acetaldehyde hemiacetal and [1α-hydroxy-3β-(3S-tetrahydropyranyloxy-trans-1-octenyl)-4α-tetrahydropyranyloxycyclopent-1α-yl] acetaldehyde hemiacetal.

9 Claims, No Drawings

NOVEL PROSTAGLANDIN INTERMEDIATES AND PROCESS FOR THE PRODUCTION THEREOF

This is a division of application Ser. No. 541,188, filed Jan. 15, 1975, now Patent No. 3,998,852, which is in turn a division of application Ser. No. 351,312, filed April 16, 1973, now U.S. Pat. No. 3,886,185, issued May 27, 1975.

This invention relates to novel prostaglandin intermediates and process for the production thereof.

More particularly, this invention relates to novel intermediates and process for the production of the compounds of Formula (15), depicted below, (dl)-[1α-hydroxy-3β-(3S-tetrahydropyranyloxy-trans-1-octenyl)-4α-tetrahydropyranyloxycyclopent-1α-yl] acetaldehyde hemiacetal, and [1α-hydroxy-3β-(3S-tetrahydropyranyloxy-trans-1-octenyl)-4α-tetrahydropyranyloxycyclopent-1α-yl] acetaldehyde hemiacetal, which are known materials useful in the production of novel dehydro analogs of the $PGE_2$ and $PGF_2$ series as disclosed in copending U.S. application Ser. No. 204,769, filed Dec. 3, 1971, now abandoned.

The novel prostaglandin intermediates and process for the production thereof are illustrated by the following flow sheet:

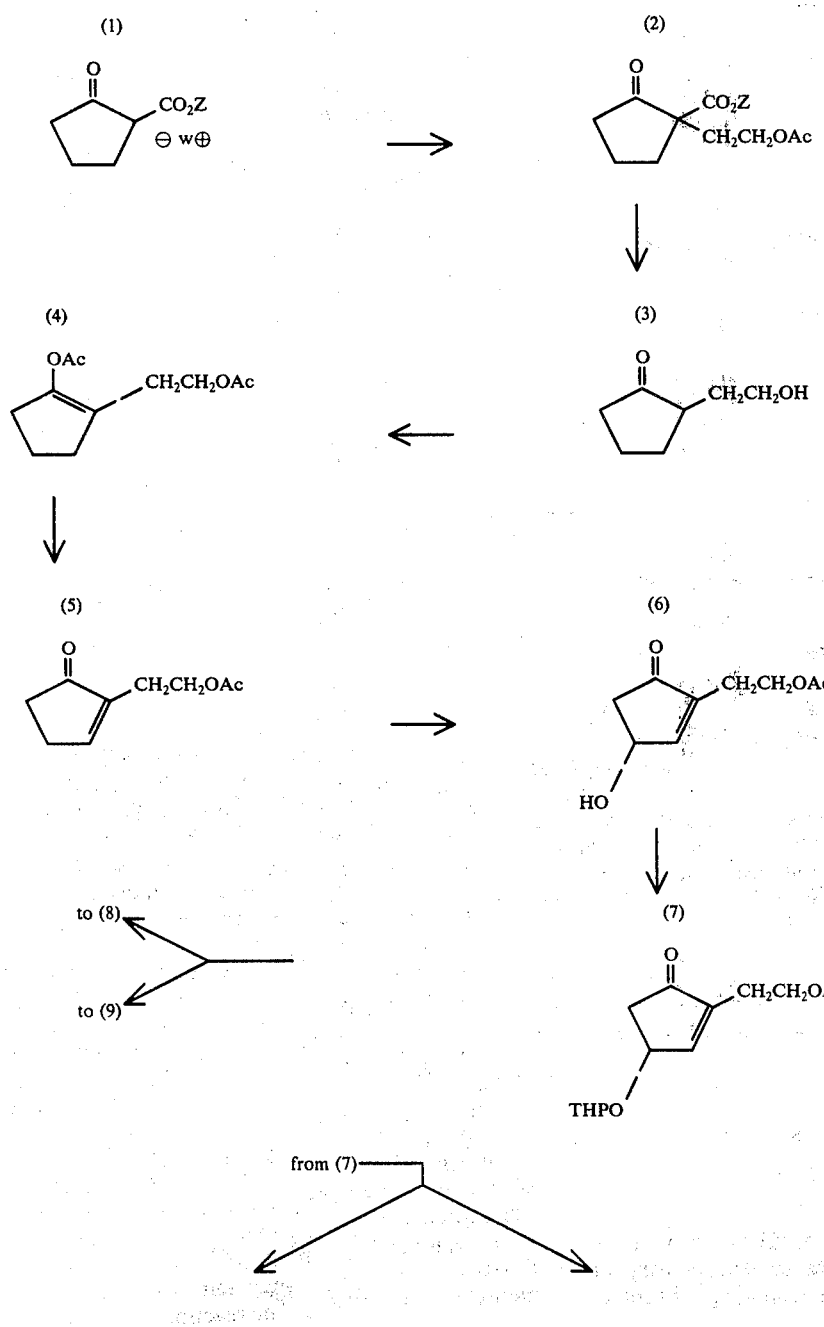

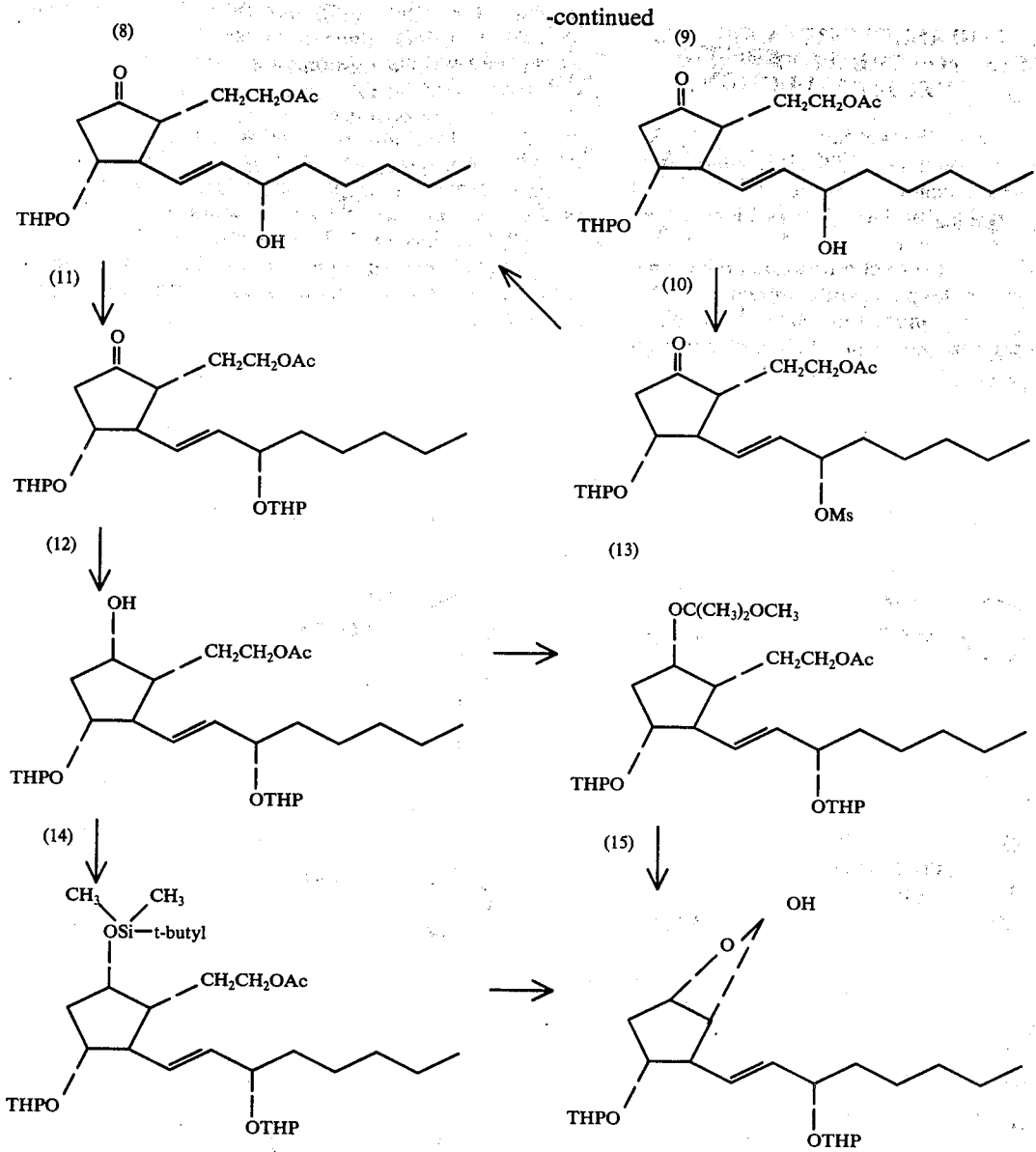

wherein W is an alkali metal, Z is methyl and ethyl, Ac is acetyl, THP is tetrahydropyranyl, Ms is mesyl, and the wavy line ($\epsilon$) represents the $\alpha$ or $\beta$ configuration or mixtures thereof.

It is to be understood and will be apparent to those skilled in the art that the compounds of Formulas (6) through (15) exist as (dl) pairs; thus, the mirror image of the compounds of Formulas (6) through (15), though not shown, are encompassed by Formulas (6) through (15) depicted above.

The compounds described herein are named as derivatives of cyclopentane and the numbering around the cyclopentane ring has been assigned as shown by the following formula:

The use of the symbol "S" or "R" preceding a substituent designates the absolute stereochemistry of that substituent according to the Cahn-Ingold-Prelog rules [see Cahn et al., Angew, Chem. Inter. Edit., Vol. 5, p. 385 (1966), errata p. 511; Cahn et al., Angew. Chem., Vol. 78, p. 413 (1966); Cahn and Ingold, J. Chem. Soc. (London), 1951, p. 612; Cahn et al., Experientia, Vol. 12, p. 81 (1956); Cahn, J. Chem. Educ., Vol. 41, p. 116 (1964)]. Because of the interrelation of the designated substituent with the other substituents in the compound having $\alpha$ or $\beta$ prefixes, the designation of the absolute configuration of one substituent fixes the absolute configuration of all substituents in the compound and thus the absolute configuration of the compound as a whole.

In practicing the above-depicted process, the compounds of Formula (1), the alkali metal salts of the methyl or ethyl (or mixtures thereof) esters of carboxy cyclopentanone, are subjected to alkylation using a 2-haloethyl acetate, preferably 2-bromoethyl acetate, to obtain the compounds of Formula (2), the methyl or ethyl esters (or mixtures thereof) of 2-(2-acetoxyethyl)-1-oxocyclopentanecarboxylate. Ordinarily, it is preferred to use the potassium salt and a mixture of the methyl and ethyl esters. The reaction is carried out in an inert solvent, e.g., dimethylsulfoxide, dimethylformamide, tetrahydrofuran, and the like, preferably dimethylsulfoxide, at a temperature of from about 20° to 100° C., for from about 16 to 48 hours, preferably 18 to 24 hours.

The compounds of Formula (2) are converted to the compounds of Formula (3), 2-(2-hydroxyethyl)-1-oxocyclopentane, by decarboxylation with a concentrated mineral acid, e.g., sulfuric, hydrochloric, hydrobromic, phosphoric, perchloric, and the like, preferably concentrated sulfuric acid. This reaction is advantageously carried out in the presence of water and an inert organic solvent, e.g., ethanol, ethylene glycol, and the like, at a temperature of from about 70° to 150° C., for from about 14 to 48 hours. The compound of Formula (3) can be isolated by conventional methods. It is preferred to eliminate the organic solvent by vacuum distillation and extract the aqueous phase containing the compound of Formula (3) with an organic solvent, e.g., isopropyl acetate, ethyl acetate, dichloromethane, and the like, and use it, as the organic extract, in the next step.

The organic extract containing the compound of Formula (3) is then treated with acetic anhydride, in the presence of a catalyst, e.g., p-toluenesulfonic acid, sulfuric acid, and the like, to yield the compound of Formula (4), 1-acetoxy-2-(2-acetoxyethyl)-cyclopent-1-ene. This reaction is advantageously monitored by thin-layer chromatography.

The compounds of Formula (4) are then brominated with a positive source of bromine, e.g., N-bromoacetamide, N-bromosuccinimide, and the like, at a temperature of from about 0° to 25° C., for from about 45 minutes to 5 hours, followed by dehydrobromination in the presence of an organic base, e.g., pyridine, collidine, and the like, and an alkali metal carbonate, e.g., lithium carbonate, at a temperature of from about 50° to 100° C. to yield the compound of Formula (5), 2-(2-acetoxyethyl)-1-oxocyclopent-2-ene. Advantageously, the reactions for the conversion of the compound of Formula (4) to the compound of Formula (5) are carried out in an inert atmosphere, e.g., nitrogen or argon, preferably nitrogen.

The compound of Formula (5) is then allylically brominated with a brominating agent, e.g., N-bromosuccinimide, in the presence of an inert orgaic solvent, e.g., carbon tetrachloride, and the like, and irradiated with visible light, at reflux temperature, for from about 60 to 120 minutes in an inert atmosphere, e.g., nitrogen. Following filtration and removal of the solvent the oily residue remaining is solvolyzed with, for example, a slight excess of silver perchlorate in a mixture of water and acetone at a temperature of from about 0° to 25° C., for from about 45 minutes to 3 hours, to yield the compounds of Formula (6), (dl)-2-(2-acetoxyethyl)-4α-hydroxy-1-oxocyclopent)-2-ene.

The compounds of Formula (6) are then etherified with dihydropyran, in the presence of an acid catalyst, e.g., phosphorous oxychloride, sulfuric acid, p-toluenesulfonic acid, and the like, in an inert organic solvent, e.g., benzene, dichloromethane, and the like, and at a temperature of from about 0° to 35° C., for from about 1 to 20 hours, to obtain the compounds of Formula (7), (dl)-2-(2-acetoxyethyl)-4α-tetrahydropyranyloxy-1-oxocyclopent-2-ene.

The compounds of Formula (7) are then reacted with a (dl)-octenol ether copper (I) lithium reagent (described more fully in Examples 7 and 7') to add the side chain at the 3-position of the cyclopentane nucleus, yielding the compounds of Formulas (8) and (9), (dl)-2α-(2-acetoxyethyl)-3β-(3S-hydroxy-trans-1-octenyl)-4α-tetrahydropyranyloxy-1-oxocyclopentane and (dl)-2α-(2-acetoxyethyl)-3β-(3R-hydroxy-trans-1-octenyl)-4α-tetrahydropyranyloxy-1-oxocyclopentane, respectively, which are separated by methods known in the art, e.g., chromatography on silica gel. This reaction is carried out at temperatures of from about −78° to −15° C., for from about 1 to 5 hours, and advantageously in an inert atmosphere, e.g., nitrogen.

The compounds of Formula (9) are converted to the compounds of Formula (10), which are in turn converted to the compounds of Formula (8), thus effecting economical utilization of materials when the (dl)-octenol ether copper (I) lithium reagent is used.

The compounds of Formula (9) are then mesylated with mesyl chloride, in the presence of an organic solvent, e.g., pyridine or a mixture of triethylamine-dichloromethane, and the like, according to methods known in the art for the production of mesyloxy compounds, to obtain the compounds of Formula (10), (dl)-2α-(2-acetoxyethyl)-3β-(3R-mesyloxy-trans-1-octenyl)-4α-tetrahydropyranyloxy-1-oxocyclopentane.

Solvolysis of the compounds of Formula (10) with a slight excess of silver perchlorate in a mixture of water and acetone is productive of (dl)-2α-(2-acetoxyethyl)-3β-(3S-hydroxy-trans-1-octenyl)-4α-tetrahydropyranyloxy-1-oxocyclopentane (8).

The compounds of Formula (8) are etherified to the compounds of Formula (11), (dl)-2α-(2-acetoxyethyl)-3β-(3S-tetrahydropyranyloxy-trans-1-octenyl)-4α-tetrahydropyranyloxy-1-oxocyclopentane under conditions similar to those described above for the conversion of the compound of Formula (6) to the compounds of Formula (7).

The compounds of Formula (11) are treated with a reducing agent, e.g., lithium perhydro-9b-boraphenalylhydride, thexyl tetrahydrolimonyl lithium borohydride, lithium tri-sec.-butyl-borohydride, and the like, in an inert anhydrous organic solvent, e.g., tetrahydrofuran, at a temperature of from about −120° to −70° C., for from about 45 minutes to 3 hours, to obtain the compounds of Formula (12), (dl)-2α-(2-acetoxyethyl)-3β-(3S-tetrahydropyranyloxy-trans-1-octenyl)-4α-tetrahydropyranyloxy-1α-hydroxycyclopentane.

The compounds for Formula (12) are then etherified with isopropenyl ether, in the presence of a mild acid catalyst, e.g., phosphorous oxychloride, p-toluenesulfonic acid, and the like, at a temperature of from about 0° to 25° C., for from about 10 minutes to 1 hour, and also in the presence of an organic base, e.g., triethylamine, to obtain the compounds of Formula (13), (dl)-2α-(2-acetoxyethyl)-3β-(3S-tetrahydropyranyloxy-trans-1-octenyl)-4α-tetrahydropyranyloxy-1α-(2-methoxyprop-2-oxy)-cyclopentane.

The compounds of Formula (13) are then hydrolyzed with a base, e.g., potassium carbonate, in a hydroxylic solvent, e.g., methanol or ethanol at a temperature of from about 0° to 35° C., for from about 3 to 15 hours, followed by treatment with an oxidizing agent, e.g., Collins reagent [chromium trioxide, pyridine and dichloromethane; Collins et al., Tetrahedron Letters, p. 3363 (1968)], or Moffatt's reagent [N, N'-diethylcarbodiimide-dimethylsulfoxide; Plitzner and Moffatt, J. A. C. S., Vol. 37, p. 1762 (1966)]: or oxidation utilizing complexes of an organic sulfide, such as methyl sulfide or phenyl methyl sulfide with N-chlorosuccinimide in dichloromethane [Corey et al., J. Org. Chem., Vol. 38, p. 1233 (1973)], and treatment with a mild acid, e.g., aqueous acetic acid, and the like, in an inert organic solvent, e.g., diethyl ether, dichloromethane, and the like, at a temperature of from about 0° to 25° C., for from about 20 minutes to 1 hour, to obtain the compounds of Formula (15), (dl)-[1α-hydroxy-3β-(3S-tetrahydropyranyloxy-trans-1-octenyl)-4α-tetrahydropyranyloxycyclopent-1α-yl] acetaldehyde hemiacetal.

Alternatively, the compounds of Formula (12) are treated with dimethyl-tert.-butylsilyl chloride, in the presence of an organic base, e.g., imidazole, in an inert anhydrous organic solvent, e.g., dimethylformamide, at a temperature of from about 0° to 35° C., for from about 3 to 15 hours, to obtain the compounds of Formula (14), (dl)-2α-(2-acetoxyethyl)-3β-(3S-tetrahydropyranyloxy-trans-1-octenyl)-4α-tetrahydropyranyloxy-1α-dimethyl-tert.-butylsilyloxycyclopentane.

The compounds of Formula (14) are then hydrolyzed with a base, e.g., potassium carbonate, in a hydroxylic solvent, e.g., methanol or ethanol, at a temperature of from about 0° to 35° C., for from about 3 to 15 hours, followed by treatment with an oxidizing agent, such as the Collins, Moffatt or the oxidizing complexes of Corey et al., described above, and treatment with a fluoride, e.g., tetra-n-butylammonium fluoride, in an inert organic solvent, e.g., tetrahydrofuran, at a temperature of from about 0° to 35° C., for from about 30 minutes to 2 hours, to obtain the compounds of Formula (15).

By substituting an S-octenol ether copper(I) lithium reagent, for the (dl)-octenol ether copper(I) lithium reagent, the compounds of Formula (7) are converted to the optically active 2α-(2-acetoxyethyl)-3β-(3S-hydroxy-trans-1-octenyl)-4α-tetrahydropyranyloxy-1-cxocyclopentane (8A).

(8A) can then be substituted for the compounds of Formula (8) and carried through the series of reactions described above [excluding, of course, those of Formula (9) → Formula (10) → Formula (8)], and exemplified below, to obtain [1α-hydroxy-3β-(3S-tetrahydropyranyloxy-trans-1-octenyl)-4α-tetrahydropyranyloxycyclopent-1α-yl] acetaldehyde hemiacetal (15A).

It is to be understood that isolation of the novel intermediates described herein can be effected by any suitable separation or purification procedure, such as, for example, extraction, filtration, evaporation, distillation, crystallization, thin-layer chromatography or column chromatography, or a combination of these procedures. Illustrations of suitable separation and isolation procedures can be had by reference to the examples described herein below. However, other equivalent separation or isolation procedures could, of course, also be used.

A further understanding of the invention can be had from the following non-limiting examples. Also, where necessary, examples are repeated to provide starting materials for subsequent examples.

EXAMPLE 1

A solution of 555 grams of the potassium salt of a mixture of the methyl and ethyl esters of carboxy cyclopentanone (1) in 4.23 liters of dimethylsulfoxide is treated with 472 grams of 2-bromoethyl acetate at 20° C. The mixture is allowed to stand at 20° C. for 20 hours, poured into 20 liters of water and extracted with four 6-liter portions of dichloromethane. The dichloromethane extracts are combined, washed with three 3-liter portions of water, and the solvent is then removed by distillation. The high boiling residue is then distilled under high vacuum to yield 577 g. of the methyl and ethyl esters of 2-(2-acetoxyethyl)-1-oxocyclopentanecarboxylate (2).

EXAMPLE 2

A solution of 557 grams of methyl and ethyl esters of 2-(2-acetoxyethyl)-1-oxocyclopentanecarboxylate in 2 liters of ethanol and 2 liters of water is treated with 14 ml. of concentrated sulfuric acid. The mixture is then boiled for 16 hours and the ethanol is eliminated by distillation under reduced pressure. The water solution of 2-(2-hydroxyethyl)-1-oxocyclopentane (3) is then saturated with sodium chloride and extracted four to ten times with 1-liter portions of isopropyl acetate. The isopropyl acetate extracts are then combined, followed by washing with two 1-liter portions of water, and drying over anhydrous potassium sulfate. The combined extracts are used directly in Example 3.

EXAMPLE 3

The combined extracts from Example 2, containing 2-(2-hydroxyethyl)-1-oxocyclopentane, is treated with 4 liters of acetic anhydride and 3 grams of p-toluenesulfonic acid, and the isopropyl acetate is distilled under vacuum at 40° to 60° C. The residue is then distilled slowly at atmospheric pressure, using a Vigreaux column, replacing from time to time the same volume of acetic anhydride-acetic acid that has been distilled. The reaction mixture is monitored by thin-layer chromatography and when the reaction is shown to be complete (8 to 11 hours) 3 grams of triethylamine is added, followed by cooling to 20° C. The acetic anhydride is distilled, using a Vigreaux column, under vacuum. The high boiling residue is distilled under high vacuum yielding 349 g. of 1-acetoxy-2-(2-acetoxyethyl)-cyclopent-1-ene (4).

EXAMPLE 4

To a solution of 72 g. of 1-acetoxy-2-(2-acetoxyethyl)-cyclopent-1-ene (4) in 935 ml. of tetrahydrofuran and 47 ml. of water, cooled to 6° C., there is added in approximately five equal portions 81 g. of solid N-bromoacetamide. The reaction mixture is stirred in the dark at 6° to 17° C. for 60 minutes under nitrogen. The reaction mixture is poured into 900 ml. of saturated aqueous sodium chloride and extracted with three 350 ml. portions of dichloromethane. The dichloromethane extracts are combined, washed with 110 ml. of saturated aqueous sodium chloride, dried over anhydrous sodium sulfate and filtered to give a filtrate to which there is added 90 ml. of pyridine. The thus-obtained solution is then reduced to a volume of 450 ml. under vacuum, placed into a 2 liter three necked flask and 645 ml. of pyridine and 63 g. of lithium carbonate are added thereto with stirring. The reaction mixture is vacuum purged with nitrogen, and heated until the internal temperature of the reaction mixture reaches 75° C. and a volume of 620 ml. is reached, followed by heating at 100° C. for 45 minutes, under nitrogen. The mixture is then vacuum distilled to a final volume of 225 ml., cooled to 20° C. and poured into saturated aqueous sodium chloride and extracted with three 380 ml. portions of dichloromethane. The combined extracts are washed with 110 ml. of aqueous sodium chloride, dried over anhydrous sodium sulfate and the solvents removed under vacuum. The high boiling residue is then distilled under high vacuum to yield 44.9 g. of 2-(2-acetoxyethyl)-1-oxocyclopent-2-ene (5).

EXAMPLE 5

A. To a solution of 50 g. of 2-(2-acetoxyethyl)-1-oxocyclopent-2-ene (5) in 900 ml. of carbon tetrachloride there is added 54.4 g. of freshly crystallized N-bromosuccinimide. The mixture is then irradiated with visible light under nitrogen and reflux for 80 minutes. The reaction mixture is cooled to 20° C. and filtered. The solvent is then removed under reduced pressure at 30° to 40° C. to yield an oily residue which is used without further purification in part (B).

B. The oily residue, obtained according to the procedure of Part (A) above is dissolved in 500 ml. of acetone and 60 ml. of water, followed by cooling of the mixture to 5° C. Under a nitrogen atmosphere, 64.6 g. of silver perchlorate is added thereto, and the mixture is stirred at 5° to 20° C. for 60 minutes. 70 G. of solid sodium bicarbonate is added and the mixture stirred for ten minutes. The precipitated silver bromide and other salts are filtered off through a layer of diatomaceous earth and the cake is washed with 200 ml. of acetone. The acetone and water are eliminated from the filtrate under reduced pressure at 30° to 40° C. The oil thus-obtained is dissolved in 100 ml. of acetone, diluted with 1.9 liters of dichloromethane and chromatographed on a column containing 500 g. of silica gel. Elution with dichloromethane-acetone yields 38.6 g. of (dl)-2-(2-acetoxyethyl)-4α-hydroxy-1-oxocyclopent-2-ene (6).

EXAMPLE 6

To a solution of 50 ml. of benzene containing 1.5 molar equivalents of distilled dihydropyran there is added 2.0 g. of 2-(2-acetoxyethyl)-4α-hydroxy-1-oxocyclopent-2-ene (6) and a drop of phosphorous oxychloride. The thus-obtained reaction mixture is stirred at 20° C. for 15 hours and following the addition of 0.5 ml. of triethylamine poured into 75 ml. of saturated aqueous sodium chloride and extracted with two 100 ml. portions of ethyl acetate. The ethyl acetate extracts are combined, washed with two 50 ml. portions of water, dried over anhydrous sodium sulfate and concentrated under reduced pressure to give (dl)-2-(2-acetoxyethyl)-4α-tetrahydropyranyloxy-1-oxocyclopent-2-ene (7).

EXAMPLE 7

To a solution of 2.94 g. of (dl)-trans-1-iodo-3-(2-methoxyprop-2-oxy)-1-octene in 10 ml. of anhydrous diethyl ether cooled to −75° C. under an atmosphere of nitrogen there is added two molar equivalents of 2.34 M solution of tert-butyl lithium in 77 ml. of pentane, followed by stirring at −75° C., under nitrogen, for two hours.

To the ethereal solution obtained above, there is added one molar equivalence of a solution of a 2:1 complex of hexamethylphosphorous triamide and 1-pentynyl copper in 40 ml. of diethyl ether at −78° C., under nitrogen, to yield the yellow mixed solution of the (dl)-octenol ether copper (I) lithium reagent which is stirred at −75° C. for 15 minutes, under nitrogen, followed by the addition of 0.75 g. (0.31 equivalents) of (dl)-2-(2-acetoxyethyl)-4α-tetrahydropyranyloxy-1-oxocyclopent-2-ene (7) in seven ml. of dry diethyl ether. The thus-obtained reaction mixture is stirred for one hour at −75° C., under nitrogen, and poured into a solution containing 30 ml. of glacial acetic acid and 70 ml. of water. Stirring is continued at 20° C. for five minutes followed by the addition of 10 g. of ammonium sulfate and stirring is continued for 30 minutes. 100 Ml. of diethyl ether is added to the reaction mixture, followed by stirring for 5 minutes and filtration over diatomaceous earth. The filter cake is washed with 30 ml. of diethyl ether and this ether washing is combined with the original filtrate. The ethereal phase is then separated from the aqueous phase and the latter is saturated with sodium chloride and extracted with 100 ml. of diethyl ether. This latter extract is combined with the ethereal phase separated above and washed successively with two 50 ml. portions of aqueous saturated sodium chloride and two 50 ml. portions of water, dried over anhydrous sodium sulfate and evaporated in vacuo, using toluene to azeotrope off the acetic acid. The solution remaining is chromatographed on a silica gel column and eluted with ethyl acetate-hexane to yield (dl)-2α-(2-acetoxyethyl)-3β-(3S-hydroxy-trans-1-octenyl)-4α-tetrahydropyranyloxy-1-oxocyclopentane (8) and (dl)-2α-(2-acetoxyethyl)-3β-(3R-hydroxy-trans-1-octenyl)-4α-tetrahydropyranyloxy-1-oxocyclopentane (9).

EXAMPLE 7A

Substituting S-trans-1-iodo-3-(2-methoxyprop-2-oxy)-1-octene, prepared by Kluge et al., U.S. application Ser. No. 252,725, filed May 12, 1972, now U.S. Pat. No. 3,867,375 for (dl)-trans-1-iodo-3-(2-methoxyprop-2-oxy)-1-octene, and following the procedure of Example 7 is productive of 2α-(2-acetoxyethyl)-3β-(3S-hydroxy-trans-1-octenyl)-4α-tetrahydropyranyloxy-1-oxocyclopentane (8A).

EXAMPLE 7'

A solution of 1.825 g. of (dl)-trans-1-iodo-3-(2-methoxyprop-2-oxy)-1-octene in 4 ml. of dry n-hexane is cooled to −75° C. under an atmosphere of nitrogen and treated with 2.4 ml. of 2.34 M n-butyl lithium in n-hexane, followed by stirring under nitrogen at −75° C. for 20 minutes. To this reaction system (at −75° C. and under nitrogen) there is added 1.14 g. of tetrakis [iodo(tri-n-butylphosphine)copper(I)] in 20 ml. of anhydrous diethyl ether. The thus-obtained solution of the (dl)-octenol ether copper(I) lithium reagent is stirred at −75° C. for 5 minutes, followed by the addition of a solution of 0.510 g. of (dl)-2-(2-acetoxyethyl)-4α-tetrahydropyranyloxy-1-oxocyclopent-2-ene (7) in 3 ml. of diethyl ether. The reaction mixture is stirred at −75° C. under nitrogen for 30 minutes, warmed to −20° C., poured into a solution of 15 ml. of glacial acetic and 35 ml. of water, and stirred at 20° C. for 30 minutes. The lower aqueous phase is then extracted with three 75 ml. portions of diethyl ether. The ethereal extracts are combined and the combined extracts are washed successively with two 50 ml. portions of saturated sodium bicarbonate and two 50 ml. portions of sodium chloride, followed by drying over anhydrous sodium sulfate. Evaporation in vacuo yields 2.57 g. of an oil which is taken up in 20 ml. of ethyl acetate-hexane and chromatographed on a silica gel column, eluting with ethyl, acetate-hexane to yield (dl)-2α-(2-acetoxyethyl)-3β-(3S-hydroxy-trans-1-octenyl)-4α-tetrahydropyranyloxy-1-oxocyclopentane (8) and (dl)-2α-(2-acetoxyethyl)-3β-(3R-hydroxy-trans-1-octenyl)-4α-tetrahydropyranyloxy-1-oxocyclopentane (9).

EXAMPLE 7'A

Substituting S-trans-1-iodo-3-(2-methoxyprop-2-oxy)-1-octene, prepared by Kluge et al., U.S. application Ser.

No. 252,725, filed May 12, 1972, now U.S. Pat. No. 3,867,375 for (dl)-trans-1-iodo-3-(2-methoxyprop-2-oxy)-1-octene, and following the procedure of Example 7' is productive of 2α-(2-acetoxyethyl)-3β-(3S-hydroxy-trans-1-octenyl)-4α-tetrahydropyranyloxy-1-oxocyclopentane (8A).

EXAMPLE 8

A solution of 10 g. of (dl)-2α-(2-acetoxyethyl)-3β-(3R-hydroxy-trans-1-octenyl)-4α-tetrahydropyranyloxy-1-oxocyclopentane (9), prepared in Example 7 or 7', in 100 ml. of pyridine, is cooled to 0° C. by means of an external ice-water-sodium chloride bath and 10% molar excess of mesyl chloride is added dropwise over a period of 15 minutes. The reaction mixture is allowed to come to 20° C., stirred for 30 minutes, poured into 2 liters of water, brought to pH 8 by the careful addition of 0.2N hydrochloric acid and extracted with three 500 ml. portions of dichloromethane. The extracts are combined and backwashed with two 200 ml. portions of water, dried over anhydrous sodium sulfate and the solvent eliminated under reduced pressure at 10° to 20° C. to yield (dl)-2α-(2-acetoxyethyl)-3β-(3R-mesyloxy-trans-1-octenyl)-4α-tetrahydropyranyloxy-1-oxocyclopentane (10).

EXAMPLE 9

A solution of 5 g. of (dl)-2α-(2-acetoxyethyl)-3β-(3P-mesyloxy-trans-1-octenyl)-4α-tetrahydropyranyloxy-1-oxocyclopentane (10) in 50 ml. of acetone containing 15 ml. of water is cooled to 5° to 10° C. by means of an external ice-water bath and then treated with a 5% excess of solid silver perchlorate. The mixture is stirred for 20 minutes and an excess of solid sodium bicarbonate is added to neutralize the liberated perchloric acid. The salts are filtered off and the filtrate concentrated to an oil under reduced pressure. The residue is chromatographed on a silica gel column and eluted with ethyl acetate-hexane to yield (dl)-2α-(2-acetoxyethyl)-3β-(3S-hydroxy-trans-1-octenyl)-4α-tetrahydropyranyloxy-1-oxocyclopentane (8).

EXAMPLE 10

To a solution of 2 g. of (dl)-2α-(2-acetoxyethyl)-3β-(3S-hydroxy-trans-1-octenyl)-4α-tetrahydropyranyloxy-1-oxocyclopentane (8), prepared in Examples 7, 7' or 9, in 35 ml. of benzene containing a small drop of phosphorous oxychloride is added 1.5 molar equivalents of distilled dihydropyran. The reaction solution is stirred at 20° C. for 15 hours and following the addition of 0.5 ml. of triethylamine poured into 75 ml. of water and extracted with two 100 ml. portions of diethyl ether. The diethyl ether (organic) extracts are combined, washed with two 50 ml. portions of saturated aqueous sodium chloride, dried over anhydrous sodium sulfate and evaporated under reduced pressure to yield (dl)-2α-(2-acetoxyethyl)-3β-(3S-tetrahydropyranyloxy-trans-1-octenyl)-4α-tetrahydropyranyloxy-1-oxocyclopentane (11).

EXAMPLE 10A

Substituting 2α-(2-acetoxyethyl)-3β-(3S-hydroxy-trans-1-octenyl)-4α-tetrahydropyranyloxy-1-oxocyclopentane (8A), prepared in Examples 7A or 7'A, for (dl)-2α-(2-acetoxyethyl)-3β-(3S-hydroxy-trans-1-octenyl)-4α-tetrahydropyranyloxy-1-oxocyclopentane, and following the procedure of Example 10 is productive of 2α-(2-acetoxyethyl)-3β-(3S-tetrahydropyranyloxy-trans-1-octenyl)-4α-tetrahydropyranyloxy-1-oxocyclopentane (11A).

EXAMPLE 11

To a solution of 3.00 g. of (dl)-2α-(2-acetoxyethyl)-3β-3S-tetrahydropyranyloxy-trans-1-octenyl)-4α-tetrahydropyranyloxy-1-oxocyclopentane (11) in 50 ml. of dry tetrahydrofuran stirring under a nitrogen atmosphere at −75° C. there is added 70 mM of lithium perhydro-9b-boraphenalylhydride in 90 ml. of dry tetrahydrofuran dropwise over a 30 minute period and after an additional 30 minutes, 20 ml. of water is added and the reaction mixture is allowed to warm to 20° C. The reaction is diluted with 50 ml. of saturated aqueous sodium chloride and extracted with three 100 ml. portions of diethyl ether. The diethyl ether extracts are combined and washed with water until neutral (pH 7), dried over anhydrous sodium sulfate and concentrated under reduced pressure to give an oily residue which is taken up in 5 ml. of dichloromethane and chromatographed on a column containing 50 g. of silica gel and eluted with ethyl acetate-hexane to yield (dl)-2α-(2-acetoxyethyl)-3β-(3S-tetrahydropyranyloxy-trans-1-octenyl)-4α-tetrahydropyranyloxy-1α-hydroxycyclopentane (12).

EXAMPLE 11A

Substituting 2α-(2-acetoxymethyl)-3β(3S-tetrahydropyranyloxy-trans-1-octenyl)-4α-tetrahydropyranyloxy-1-oxocyclopentane (11A) for (dl)-2α-(2-acetoxyethyl)-3β-(3S-tetrahydropyranyloxy-trans-1-octenyl)-4α-tetrahydropyranyloxy-1-oxocyclopentane and following the procedure of Example 11 is productive of 2α-(2-acetoxyethyl)-3β-(3S-tetrahydropyranyloxy-trans-1-octenyl)-4α-tetrahydropyranyloxy-1α-hydroxycyclopentane (12A).

EXAMPLE 12

To a flask containing 1.0 g. of (dl)-2α-(2-acetoxyethyl)-3β-(3S-tetrahydropyranyloxy-trans-1-octenyl)-4α-tetrahydropyranyloxy-1α-hydroxycyclopentane (12) and 1.0 g. of isopropenyl ether, a trace of phosphorous oxychloride is introduced and the flask is stoppered and stirred at 20° C. for 45 minutes, followed by the addition of 10 drops of triethylamine and concentrating under vacuum to yield an oily residue comprising (dl)-2α-(2-acetoxyethyl)-3β-(3S-tetrahydropyranyloxy-trans-1-octenyl)-4α-tetrahydropyranyloxy-1α-(2-methoxyprop-2-oxy)-cyclopentane (13) which is used without further purification.

EXAMPLE 12A

Substituting 2α-(2-acetoxyethyl)-3β-(3S-tetrahydropyranyloxy-trans-1-octenyl)-4α-tetrahydropyranyloxy-1α-hydroxycyclopentane (12A) for (dl)-2α-(2-acetoxyethyl)-3β-(3S-tetrahydropyranyloxy-trans-1-octenyl)-4α-tetrahydropyranyloxy-1α-hydroxycyclopentane and following the procedure of Example 12 is productive of an oily residue comprising 2α-(2-acetoxyethyl)-3β-(3S-tetrahydropyranyloxy-trans-1-octenyl)-4α-tetrahydropyranyloxy-1α-(2-methoxyprop-2-oxy)-cyclopentane (13A).

EXAMPLE 13

A solution of 1.808 g. of dimethyl-tert.-butylsilyl chloride and 1.702 g. of imidazole in 200 ml. of anhydrous dimethylformamide is added to 4.81 g. of (dl)-2α-(2-acetoxyethyl)-3β-(3S-tetrahydropyranyl-trans-1- octenyl)-4α-tetrahydropyranyloxy-1α-hydroxycyclopentane (12) and the reaction solution stirred at 20° C. for 12 hours. 200 Ml. of diethyl ether is added and the resultant solution is washed successively with two 50 ml. portions of aqueous sodium chloride, two 50 ml. portions of water, followed by drying of the organic phase over anhydrous sodium sulfate and evaporation under vacuum to yield (dl)-2α-(2-acetoxyethyl)-3β-(3S-tetrahydropyranyloxy-trans-1-octenyl)-4α-tetrahydropyranyloxy-1α-dimethyl-tert.-butylsilyloxycyclopentane (14).

EXAMPLE 13A

Substituting 2α-(2-acetoxyethyl)-3β-(3S-tetrahydropyranyloxy-trans-1-octenyl)-4α-tetrahydropyranyloxy-1α-hydroxycyclopentane (12A) for (dl)-2α-(2-acetoxyethyl)-3β-(3S-tetrahydropyranyloxy-trans-1-octenyl)-4α-tetrahydropyranyloxy-1α-hydroxycyclopentane in the procedure of Example 13 is productive of 2α-(2-acetoxyethyl)-3β-(3S-tetrahydropyranyloxy-trans-1-octenyl)-4α-tetrahydropyranyloxy-1α-dimethyl-tert.-butylsilyloxycyclopentane (14A).

EXAMPLE 14

A. 1.0 G. of the oily residue comprising (dl)-2α-(2-acetoxyethyl)-3β-(3S-tetrahydropyranyloxy-trans-1-octenyl)-4α-tetrahydropyranyloxy-1α-(2-methoxyprop-2-oxy)-cyclopentane (13) is added to 15 ml. of absolute methanol containing 400 mg. of potassium carbonate and stirred at 20° C. for 12 hours. The methanol is stripped out at reduced pressure and the residue remaining is extracted with 200 ml. of diethyl ether and the extract is washed with two 50 ml. portions of water. The ethereal solution is then dried over anhydrous sodium sulfate and concentrated under vacuum to yield an oily residue, which is used in part B below. B. 0.60 G. (6mM) of anhydrous chromium trioxide is added to a stirred solution of 0.949 g. of dry pyridine in 15 ml of dry dichloromethane and stirred under a dry nitrogen atmosphere at 20° C. for 15 minutes after which the oily residue, obtained in Part A above, in 5 ml. of dichloromethane is added and the reaction mixture is stirred for 30 minutes at 20° C. The solution is decanted from the residue and the residue is washed with 200 ml. of diethyl ether. The organic solutions are combined and washed successively with two 50 ml. portions of 5% aqueous sodium hydroxide, two 75 ml. portions of aqueous saturated sodium chloride and a 50 ml. portion of water. 20 Ml. of 35% aqueous acetic acid is added to the washed, combined organic solution and stirred at 20° C. for 20 minutes. The reaction mixture is then washed with 5% aqueous sodium hydroxide until basic, after which it is washed with water until neutral, dried over anhydrous sodium sulfate and evaporated under reduced pressure to yield an oily residue which is taken up in 5 ml. of dichloromethane and poured onto a chromatograhic column containing 25 g. of silica gel. The column is eluted with ethyl acetate-hexane to yield (dl)-[1α-hydroxy-3β-(3S-tetrahydropyranyloxy-trans-1-octenyl)-4α-tetrahydropyranyloxycyclopent-1α-yl] acetaldehyde hemiacetal (15).

EXAMPLE 14A

Substituting the oily residue comprising 3α-(2-acetoxyethyl)-3β-(3S-tetrahydropyranloxy-trans-1-octenyl)-4α-tetrahydropyranyloxy-1α-(2-methoxyprop-2-oxy)-cyclopentane (13A) for (dl)-2α-(2-acetoxyethyl)-3β-(3S-tetrahydropyranyloxy-trans-1-octenyl)-4α-tetrahydropyranyloxy-1α-(2-methoxyprop-2-oxy)-cyclopentane in the procedure of Example 14 is productive of [1α-hydroxy-3β-(3S-tetrahydropyranyloxy-trans-1-octenyl)-4α-tetrahydropyranyloxycyclopent-1α-yl] acetaldehyde hemiacetal (15A).

EXAMPLE 15

A. 1.0G. of (dl)-2α-(2-acetoxyethyl)-3β-(3S-tetrahydropyranyloxy-trans-1-octenyl)-4α-tetrahydropyranyloxy-1α-dimethyltert.-butylsilyloxycyclopentane (14) is added to 20 ml. of methanol containing 400 mg. of potassium carbonate and stirred at 20° C. for 15 hours. The methanol is stripped off in vacuo and the residue remaining is extracted with 200 ml. of diethyl ether and the extract is washed with two 50 ml. portions of water. The ethereal solution is then dried over anhydrous sodium sulfate and evaporated under reduced pressure to yield an oily residue, which is used in Part B below.

B. 0.60 G. of anhydrous chromium trioxide is added to a stirred solution of 0.95 g. of dry pyridine in 15 ml. of dry dichloromethane and stirred under a dry nitrogen atmosphere at 20° C. for 15 minutes after which the oily residue, obtained in Part A above, in 2 ml. of dichloromethane is added and the reaction mixture is stirred for 15 minutes at 20° C. The solution is decanted from the residue and the residue is washed with 200 ml. of diethyl ether. The organic solutions are combined and washed successively with two 50 ml. portions of 5% aqueous sodium bicarbonate, two 25 ml. portions of saturated sodium chloride, with water until neutral (pH 7), dried over anhydrous sodium sulfate and evaporated to give an oily residue. To the thus-obtained oily residue there is added a solution of 0.8 g. of tetra-n-butylammonium fluoride [Corey and Snider, J.A.C.S., Vol. 94, p. 2549 (1972)] in 8 ml. of anhydrous tetrahydrofuran. The resulting solution is stirred at 20° C. for one hour and then poured into 35 ml. of saturated aqueous sodium chloride, and extracted with three 75 ml. portions of diethyl ether. The diethyl ether extracts are combined and the combined extracts washed successively with two 30 ml. portions of aqueous sodium chloride and 30 ml. of water, dired over anhydrous sodium sulfate, evaporated in vacuo to give a residue which is chromatographed on a column containing 20 g. of silica gel which is eluted with ethyl acetate-hexane to yield (dl)-[1α-hydroxy-3β-(3S-tetrahydropyranyloxy-trans-1-octenyl)-4α-tetrahydropyranyloxycyclopent-1α-yl] acetaldehyde hemiacetal (15).

EXAMPLE 15A

Substituting 2α-(2-acetoxyethyl)-3β-(3S-tetrahydropyranyloxy-trans-1-octenyl)-4α-tetrahydropyranyloxy-1α-dimethyl-tert.butylsilyloxycyclopentane (14A) for (dl)-2α-(2-acetoxyethyl)-3β-(3S-tetrahydropyranyloxy-trans-1-octenyl)-4α-tetrahydropyranyloxy)-1α-dimethyl-tert.-butylsilyloxycyclopentane in the procedure of Example (15) is productive of [1α-hydroxy-3β-(3S-tetrahydropyranyloxy-trans-1-octenyl)-4α-tetrahydropyranyloxycyclopent-1α-yl] acetaldehyde hemiacetal (15A).

What is claimed is:

1. A compound selected from the group consisting of (dl)-2α-(2-acetoxyethyl)-3β-(3S-tetrahydropyranyloxy-trans-1-octenyl)-4α-tetrahydropyranyloxy-1-oxocyclopentane (dl)-2α-(2-acetoxyethyl)-3β-(3S-tetrahydropyranyloxy-trans-1-octenyl)-4α-tetrahydropyranyloxy-1α-hydroxycyclopentane, (dl)-2α-(2-acetoxyethyl)-3β-(3S-tetrahydropyranyloxy-trans-1-octenyl)-4α-tetrahydropyranyloxy-1α-(2-methoxyprop-2-oxy)cyclopentane, (dl)-2α-(2-acetoxyethyl)-3β-(3S-tetrahydropyranyloxy-trans-1-octenyl)-4α-tetrahydropyranyloxy-1α-dimethyl-tert.-butylsilyloxycyclopentane, 2α-(2-acetoxyethyl)-3β-(3S-tetrahydropyranyloxy-trans-1-octenyl)-4α-tetrahydropyranyloxy-1-oxocyclopentane, 2α-(2-acetoxyethyl)-3β-(3S-tetrahydropyranyloxy-trans-1-octenyl)-4α-tetrahydropyranyloxy-1α-hydroxycyclopentane, 2α-(2-acetoxyethyl)-3β-(3S-tetrahydropyranyloxy-trans-1-octenyl)-4α-tetrahydropyranyloxy-1α-(2-methoxyprop-2-oxy)-cyclopentane, and 2α-(2-acetoxyethyl)-3β-(3S-tetrahydropyranyloxy-trans-1-octenyl)-4α-tetrahydropyranyloxy-1α-dimethyl-tert.-butylsilyloxycyclopentane.

2. The compound of claim 1, (dl)-2α-(2-acetoxyethyl)-3β-(3S-tetrahydropyranyloxy-trans-1-octenyl)-4α-tetrahydropyranyloxy-1-oxocyclopentane.

3. The compound of claim 1, (dl)-2α-(2-acetoxyethyl)-3β-(3S-tetrahydropyranyloxy-trans-1-octenyl)-4α-tetrahydropyranyloxy-1α-hydroxycyclopentane.

4. The compound of claim 1, (dl)-2α-(2-acetoxyethyl)-3β-(3S-tetrahydropyranyloxy-trans-1-octenyl)-4α-tetrahydropyranyloxy-1α-(2-methoxyprop-2-oxy)-cyclopentane.

5. The compound of claim 1, (dl)-2α-(2-acetoxyethyl)-3β-(3S-tetrahydropyranyloxy-trans-1-octenyl)-4α-tetrahydropyranyloxy-1α-dimethyl-tert.-butylsilyloxycyclopentane.

6. The compound of claim 1, 2α-(2-acetoxyethyl)-3β-(3S-tetrahydropyranyloxy-trans-1-octenyl)-4α-tetrahydropyranyloxy-1-oxocyclopentane.

7. The compound of claim 1, 2α-(2-acetoxyethyl)-3β-(3S-tetrahydropyranyloxy-trans-1-octenyl)-4α-tetrahydropyranyloxy-1α-hydroxycyclopentane.

8. The compound of claim 1, 2α-(2-acetoxyethyl)-3β-(3S-tetrahydropyranyloxy-trans-1-octenyl)-4α-tetrahydropyranyloxy-1α-(2-methoxyprop-2-oxy)-cyclopentane.

9. The compound of claim 1, 2α-(2-acetoxyethyl)-3β-(3S-tetrahydropyranyloxy-trans-1-octenyl)-4α-tetrahydropyranyloxy-1α-dimethyl-tert.-butylsilyloxycyclopentane.

* * * * *